(12) United States Patent
Pavlov et al.

(10) Patent No.: US 8,142,640 B2
(45) Date of Patent: Mar. 27, 2012

(54) CHLORIDE ANALYSIS IN ACID COPPER PLATING BATHS

(75) Inventors: Michael Pavlov, Fairlawn, NJ (US);
Eugene Shalyt, Washington Township, NJ (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 904 days.

(21) Appl. No.: 11/899,787

(22) Filed: Sep. 6, 2007

(65) Prior Publication Data

US 2009/0065362 A1    Mar. 12, 2009

(51) Int. Cl.
*G01N 27/26* (2006.01)
(52) U.S. Cl. .................. 205/778.5; 205/789; 205/81
(58) Field of Classification Search .............. 205/81, 205/101, 778.5–789; 436/101, 125
See application file for complete search history.

(56) References Cited

U.S. PATENT DOCUMENTS

| | | | | |
|---|---|---|---|---|
| 5,320,724 | A * | 6/1994 | Ludwig et al. | 205/780.5 |
| 6,673,226 | B1 * | 1/2004 | Kogan et al. | 205/81 |
| 2001/0052465 | A1 * | 12/2001 | Dordi et al. | 205/95 |
| 2004/0031692 | A1 * | 2/2004 | Hardee | 205/118 |
| 2005/0241946 | A1 * | 11/2005 | Nagai et al. | 205/93 |

FOREIGN PATENT DOCUMENTS

DE        263354 A * 12/1988

OTHER PUBLICATIONS

English Equiv of DD263354A, Kriebitzsc et al. 1988, 2 pages.*
Machine translation of Kriebitzsch et al., DD263354A1, 1988, pp. 1-5.*

* cited by examiner

*Primary Examiner* — Kaj K Olsen
*Assistant Examiner* — Susan Leong
(74) *Attorney, Agent, or Firm* — D. Morgan Tench

(57) ABSTRACT

The chloride concentration in an acid copper plating bath is determined from the chloride oxidation current measured under controlled hydrodynamic conditions at a noble metal electrode using specific voltammetric parameters. The measurement is made directly on the undiluted plating bath so that the chloride measurement is fast and no waste stream is generated.

19 Claims, 8 Drawing Sheets

CHLORIDE ANALYSIS IN ACID COPPER PLATING BATHS

BACKGROUND OF THE INVENTION

1. Field of the Invention

This invention is concerned with analysis of organic additives and contaminants in plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions for which the additive concentration in the vicinity of the electrode surface is well defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R Haak, C. Ogden and D. Tench, Plating Surf. Fin. 68(4), 52 (1981) and Plating Surf. Fin. 69(3), 62 (1982)].

Acid copper sulfate electroplating baths require a minimum of two types of organic additives to provide deposits with satisfactory properties and good leveling characteristics. The suppressor additive (also called the "polymer", "carrier", or "wetter", depending on the bath supplier) is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating that would result in powdery or nodular deposits. An anti-suppressor additive (also called the "brightener", "accelerator" or simply the "additive", depending on the bath supplier) is required to counter the suppressive effect of the suppressor and provide the accelerated deposition within substrate recesses needed for leveling. Plating bath vendors typically provide additive solutions that may contain additives of more than one type, as well as other organic and inorganic addition agents. The suppressor additive may be comprised of more than one chemical species and generally involves a range of molecular weights.

Acid copper sulfate baths have functioned well for plating the relatively large surface pads, through-holes and vias found on printed wiring boards (PWB's) and have recently been adapted for plating fine trenches and vias in dielectric material on semiconductor chips. The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process shrank below 0.2 μm, it became desirable to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. Leveler additive species tend to exert a relatively strong decelerating effect on the copper electrodeposition rate but are typically present in the plating bath at very low concentration so that their decelerating effect is weaker than that of suppressor additives. Due to their low concentration, leveler species tend to function under diffusion control.

In order to attain good bottom-up filling and avoid overplating of ultra-fine chip features, the concentrations of all three additives must be accurately analyzed and controlled. The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O. Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. 70$^{th}$ Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. Pat. No. 6,572,753 to Chalyt et al.

The concentration of chloride ion in acid copper plating baths must also be closely controlled (typically at a value in the 25 to 100 mg/L range) since chloride ion is essential to the functioning of the additive system. However, chloride ion specific electrodes are not suitable for use in acid copper plating baths because of the presence of interfering species (e.g., organic additives, copper ions and strong acid) that cause the electrode potential to drift with time. Another prior art method for chloride analysis involves titration with a solution of mercuric nitrate, which is a hazardous material that requires special handling and waste disposal. The colorimetric endpoint for this titration is also difficult to detect with sufficient accuracy, especially for an automated analysis system.

An alternative prior art method for chloride analysis of acid copper plating baths involves potentiometric titration with silver nitrate solution, for which the endpoint detection is readily automated and no hazardous waste is involved. However, the silver chloride precipitate produced during the titration is difficult to remove, and residues of the precipitate, or of a reducing agent (typically, sodium thiosulfate) used to dissolve it, can interfere with subsequent analyses performed in the same cell. The CVS methods used for analyses of organic additives in acid copper baths are particularly sensitive to interference from chloride and silver ions (derived from dissolution of the silver chloride precipitate) and reducing agents, which can affect the copper electrodeposition rate. Another disadvantage of the prior art potentiometric titration method is that the silver nitrate solution is decomposed by ambient light and must be handled in darkened containers and tubing, which interfere with visual inspection of the reagent delivery system. In addition, this titration method is only moderately sensitive to chloride ion.

U.S. Pat. No. 6,673,226 to Kogan et al., which is assigned to the same assignee as the present application, describes a voltammetric method for determining the chloride concentration in an acid copper plating bath from the effect that chloride ion exerts on the copper electrodeposition rate in the presence of organic additives. The procedure involves measuring a CVS rate parameter in a background electrolyte containing at least one organic additive but substantially no chloride ion, before and after addition of a predetermined volume fraction of the plating bath sample. Although it ameliorates cross-contamination and waste disposal issues compared to prior art titration approaches, this prior art voltammetric method is time consuming and still generates a waste stream of measurement solutions.

None of these prior art methods provides the sensitivity and robustness needed for analysis of chloride ion in production acid copper plating baths without the use of contaminating or hazardous chemicals. The prior art methods also tend to be time consuming. A chloride analysis method useful for industrial acid copper plating processes, particularly those employed by the electronics industry, is needed. Major considerations in this case are reductions in the analysis time and the process waste stream. A preferred chloride analysis method would be performed directly on the acid copper bath without dilution.

In principle, the current associated with chloride oxidation at a noble metal electrode in acid copper baths might be used to determine the chloride concentration. In practice, however, interference from adsorption and oxidation of organic additives and breakdown products and from the onset of oxygen evolution has been found to interfere with chloride determination via chloride electrochemical oxidation. Consequently, previous attempts to use the chloride oxidation current for chloride analysis have failed. The inventors have discovered, however, that the chloride concentration in an acid copper plating bath may be determined from the chloride oxidation current measured under controlled hydrodynamic conditions at a noble metal electrode using specific voltammetric parameters.

SUMMARY OF THE INVENTION

The invention provides a method and an apparatus for determining the concentration of chloride ion in an acid copper plating bath sample. According to the method, the chloride concentration is determined from the chloride oxidation current measured using specific voltammetric parameters for at least one predetermined potential at a noble metal electrode as the plating bath sample is flowed at a predetermined rate over the electrode surface. The important voltammetric parameters, which are preferably optimized to provide optimum sensitivity and reproducibility for the chloride determination, include the negative potential limit, the positive potential limit, the potential scan rate, and the potential at which the chloride oxidation current is measured. It is also important that the plating bath sample be maintained at a predetermined temperature during measurement of the chloride oxidation current.

The invention further provides an apparatus for automated application of the method of the invention. The apparatus comprises a computing device that is interfaced with suitable electronic and mechanical equipment, and includes a memory element with a stored algorithm operative to effect at least the basic steps of the method of the invention.

The invention is useful for improving the quality of deposits from acid copper plating baths by providing a method and an apparatus for controlling the chloride concentration, which is critical to the functioning of the additive system. The method of the invention is especially useful for controlling the chloride concentration in acid copper baths used for plating semiconductor wafers in the Damascene process. The method of the invention may be performed rapidly, compared to prior art methods, and does not generate a waste stream.

Further features and advantages of the invention will be apparent to those skilled in the art from the following detailed description, taken together with the accompanying drawings.

DETAILED DESCRIPTION OF THE INVENTION

Figure 1:
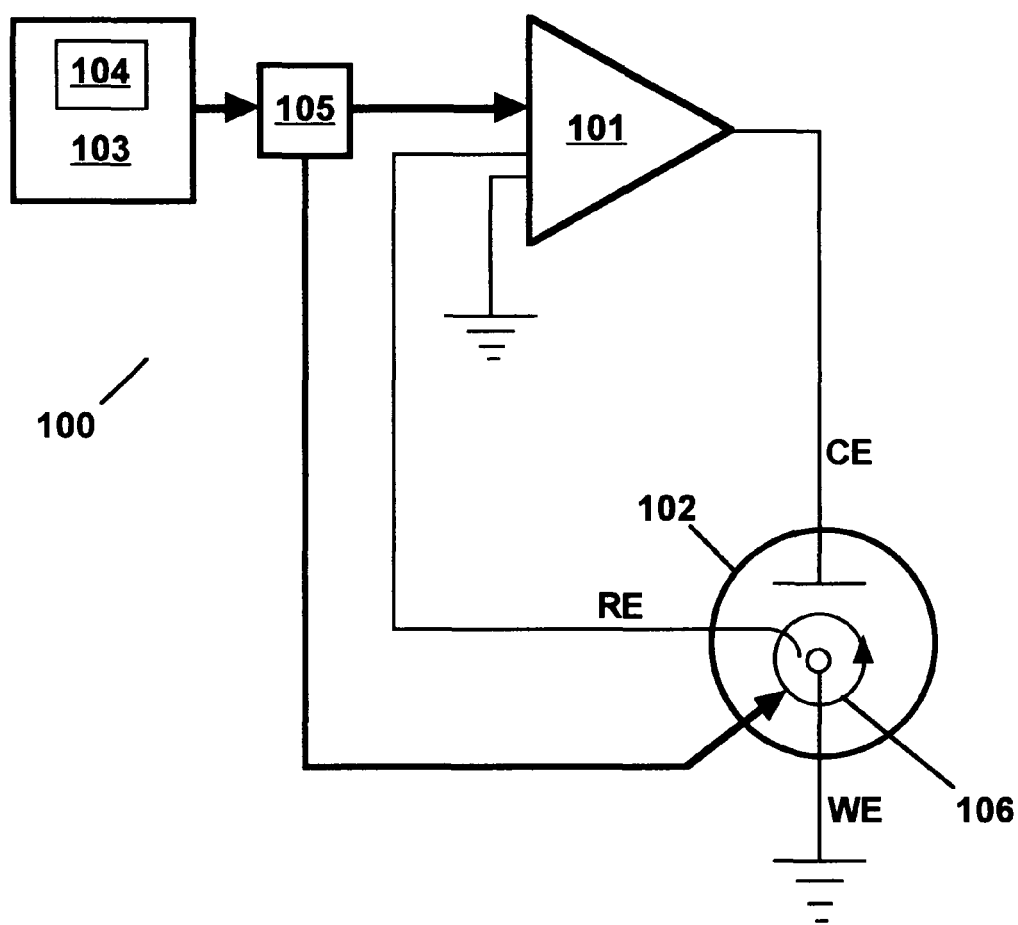
FIG. 1 is a schematic representation of a preferred apparatus of the invention.

Technical terms used in this document are generally known to those skilled in the art. The term "electrode potential", or simply "potential", refers to the voltage occurring across a single electrode-electrolyte interface. Electrode potentials reported in this document are versus a SSCE/M reference (silver-silver chloride electrode modified by replacing the solution in a standard SSCE electrode with a saturated AgCl solution also containing 0.1 M KCl and 10 volume % sulfuric acid). This electrode has a potential of +0.205 V vs. the normal hydrogen electrode (NHE). In practice, the electrode potential often includes an appreciable resistive voltage drop in the electrolyte, which typically remains constant and does not affect voltammetric analysis results obtained under the same conditions.

The terms "electroplating", "plating" and "electrodeposition" refer to copper electrodeposition and are equivalent. A "plating bath" is employed for practical copper plating and contains organic additives whose concentrations are controlled within ranges, whereas the corresponding "supporting electrolyte" typically has substantially the same inorganic composition, not including chloride ion, as the plating bath but no organic additives. A "background electrolyte" comprises a supporting electrolyte containing one or more organic additives at predetermined concentrations. The concentration of chloride ion in a supporting electrolyte or a background electrolyte may be varied.

The term "standard addition" generally means addition of a predetermined quantity of a species (chloride ion, for example) to a predetermined volume of a solution (background electrolyte, for example). The predetermined quantity may be a predetermined weight of the species or a predetermined volume of a standard solution containing the species. The terms "chloride ion" and "chloride" may be used interchangeably although, generally, "chloride ion" is used as the noun and "chloride" is used as the adjective. The symbol "M" means molar concentration. The "volume fraction" is the volume of a first solution added to a second solution divided by the total volume of the resulting solution. Calibration data are typically handled as standard curves or plots but such data may be tabulated and used directly, especially by a computer, and the terms "curve" or "plot" include tabulated data.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

The invention provides a method and an apparatus for determining the concentration of chloride ion in an acid copper plating bath sample. The invention is suitable for analysis of acid copper plating baths comprising anions selected from the group consisting of sulfate, fluoroborate, sulfamate, alkylsulfonate, and mixtures thereof.

In acid copper plating baths, chloride ion is typically present at very low concentration in the range from 20 to 100 mg/L (ppm) so that electrochemical oxidation of chloride ion generally occurs under some degree of diffusion control. If a plating bath sample is flowed over the electrode surface at a constant flow rate to establish constant hydrodynamic conditions at the electrode surface, the chloride oxidation current exhibits a diffusion-limited plateau (at sufficiently positive potentials) corresponding to oxidation of chloride ions as quickly as they reach the electrode surface via diffusion across the electrode diffusion layer. In this case, the chloride oxidation current is directly proportional to the concentration of chloride ion in the plating bath sample, and may be used to determine the bath chloride concentration provided that the effects of interfering factors can be adequately suppressed or avoided.

According to the method of the invention, the chloride concentration is determined from the chloride oxidation current measured using specific voltammetric parameters for at least one predetermined potential at a noble metal electrode as the plating bath sample is flowed at a predetermined rate over the electrode surface. The plating bath sample is preferably un-diluted, but may be diluted by standard addition of the supporting electrolyte or a background electrolyte containing no chloride ion or a known concentration of chloride ion.

The basic steps of the method of the invention for determining the concentration of chloride ion in an acid copper plating bath sample, comprise: (1) flowing the plating bath sample at a constant predetermined flow rate over the surface of a working electrode comprising a noble metal; (2) scanning the potential of the working electrode relative to a reference electrode between a predetermined negative potential limit and a predetermined positive potential limit at a predetermined potential scan rate; and (3) measuring at least one chloride oxidation current for at least one predetermined working electrode potential in a predetermined potential range to provide a chloride current parameter. The chloride current parameter provided in Step (3) may be used as a relative measure of the chloride concentration in the acid copper plating bath sample.

The method of the invention may further comprise the steps of: (4) generating a standard curve by repeating Steps (1)-(3) of the method for a plurality of chloride standard solutions comprising a background electrolyte of the plating bath sample with different known concentrations of chloride ion; and (5) comparing the chloride current parameter provided in Step (3) of the method with the standard curve to determine the concentration of chloride ion in the plating bath sample. Step (4) is a calibration step that allows the chloride concentration to be expressed in normal concentration units. The plating bath sample and the standard solutions preferably comprise the same organic additives at the same predetermined concentrations within the normal additive control ranges for the plating bath.

The working electrode preferably comprises platinum but may comprise another noble metal, for example, iridium, gold, osmium, palladium, rhenium, rhodium, ruthenium, and alloys thereof and with platinum. The term "noble" denotes a metal that is electrochemically stable in the acid copper plating bath over the potential range between the negative and positive potential limits used for the chloride determination.

The plating bath sample may be flowed over the working electrode surface by any suitable means that provides a constant flow rate, and preferably laminar flow. Laminar flow is preferred since turbulence disrupts the diffusion layer at the electrode surface and may introduce errors in the chloride determination. As known to those skilled in the art, turbulence may be avoided by selecting a suitable electrode geometry and avoiding excessively high flow rates. Suitable means for flowing the plating bath sample over the working electrode surface at a constant flow rate include use of a rotating disk electrode, or pumping the plating bath sample at a constant rate past a stationary working electrode. Suitable liquid pumps that provide a constant flow rate are well known in the art. The range of flow rates providing acceptable results depends on the electrode geometry and cell characteristics. For a typical system, flow rates in the range from 200 to 300 mL/minute gave good results.

A rotating disk electrode rotating at a constant rate provides solution flow over the electrode surface at a constant rate (neglecting minor non-uniformity over the disk surface). For convenience, solution flow rate is typically expressed in terms of the electrode rotation rate, which precisely defines the thickness of the diffusion layer at the electrode surface. A typical rotating disk electrode comprises a platinum metal disk (3-5 mm diameter), with an electrical contact wire on the backside, embedded flush with one end of an insulating plastic cylinder (10-20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). A properly designed rotating disk electrode can be used from about 100 rpm (below which control of the rotation rate tends to be difficult) up to about 10,000 rpms (above which turbulence occurs for aqueous solutions). For the chloride determination of the invention, the electrode rotation rate is preferably in the range from 200 to 3000 rpm.

The key voltammetric parameters, which are preferably optimized to provide optimum sensitivity and reproducibility for the chloride determination, include the negative potential limit, the positive potential limit, and the potential scan rate. The negative potential limit is preferably less negative than for CVS additive analyses to minimize adsorption and electrochemical reaction of organic additives and additive breakdown products that would be electrochemically oxidized in the same potential range as chloride ion during the positive scan. In addition to introducing extraneous oxidation currents, adsorbed organic additives and breakdown products may also introduce errors in the chloride determination by partially blocking the working electrode surface, resulting in reduced chloride oxidation currents. The positive potential limit is preferably not so positive that excessive oxygen evolution interferes with attaining a steady-state condition for the working electrode surface. The potential scan rate is also important since it determines the time available for adsorption, desorption and reaction of the various solution species, additives and chloride ion, for example, in a given potential range. These voltammetric parameters are preferably optimized in an iterative process since their effects are interdependent. Preferably, the voltammetric parameters are optimized for each type of acid copper plating bath having a different additive system.

Another voltammetric parameter of importance is the working electrode potential at which the chloride oxidation current is measured. An approximate potential range for this measurement may be determined by inspection of the chloride oxidation region of cyclic voltammograms measured (using optimized voltammetric parameters) for plating bath samples containing different chloride concentrations. The range of suitable potentials for measuring the chloride oxidation current generally includes the middle of the range over which chloride oxidation current is evident. The optimum potential range for measuring the chloride oxidation current is determined empirically.

In a preferred embodiment, the chloride concentration in a plating bath sample is determined by cycling the potential of a platinum disk electrode, rotating at 2500 rpm, between $-0.10$ V (or a more positive potential) and $+1.65$ V vs. SSCE/M at 2.00 V/s in the plating bath sample, and measuring at least one steady-state current on the positive scan at a potential or potentials around $+1.46$ V vs. SSCE/M. These voltammetric parameter values were found to provide good sensitivity, accuracy and reproducibility for determination of the chloride concentration in the Low Acid Viaform™ (Enthone, Inc.) acid copper sulfate plating bath at 25° C. Significant variation in one or more of these parameters may be required to optimize results for other plating bath temperatures, or for other acid copper plating baths, especially those employing a different additive system. Variations in the voltammetric parameters and/or temperature that provide adequate results for a given plating bath are within the scope of the invention.

Nonetheless, specific voltammetric parameter limits for practicing the invention may be defined for ambient temperatures. In particular, the negative potential limit must be less negative than $-0.15$ V vs. SSCE/M and the positive potential limit must be less positive than $+1.70$ V vs. SSCE/M. Good results were obtained for negative potential limits of $-0.10$ and $+0.17$ V vs. SSCE/M. The optimum potential scan rate is generally in the range from 1.0 to 4.0 V/second. The chloride oxidation current may be measured at a potential in the range from 1.3 to 1.5 V vs. SSCE/M. Within the scope of the invention, the chloride oxidation current may be measured at any potential or range of potentials that yields reproducible results for the chloride determination. It may be advantageous with respect to the chloride determination for the chloride current parameter to be the average of a plurality of chloride oxidation currents, measured at the same potential or at a plurality of working electrode potentials.

It is important that the plating bath sample and the standard solutions be maintained at the same predetermined temperature during measurements of the chloride oxidation currents since errors resulting from temperature variations may be significant. The level of temperature control needed depends of the required accuracy for the chloride determination. In some cases, temperature control within $\pm 1°$ C. may be adequate but control within less than $\pm 0.5°$ C. is typically needed. Preferably, the plating bath sample and the standard solutions are maintained at the predetermined temperature within $\pm 0.1°$ C. during chloride oxidation current measurements. Acid copper baths are typically operated at ambient temperature but voltammetric measurements on a plating bath sample may be made at a higher or a lower temperature. The accuracy of chloride oxidation current measurements may be improved by employing a slightly elevated solution temperature (3° or 4° C. above room temperature, for example) that can be more consistently maintained. Equipment for controlling the temperature of electrochemical cells is well known in the art.

Other factors that tend to affect the reproducibility and accuracy of the chloride determination of the invention are variations in the concentrations of organic additives and acid (sulfuric acid, for example) in the plating bath sample. Although optimization of the voltammetric parameters reduces the effects of organic additives on the chloride determination, organic additive concentrations are preferably maintained within their normal control ranges in the plating bath sample to further reduce their effects. This is generally not an issue since close control of the concentrations of additives in acid copper plating baths is normally necessary anyway to provide good deposit properties. Standard chloride solutions used for calibration should contain the same additives at the same concentrations as in the plating bath sample.

Likewise, optimization of the voltammetric parameters and close control of the acid concentration in production plating baths reduce the effects of variations in the acid concentration on the chloride determination. If necessary, the effects of variations in the acid concentration in the plating bath sample can be taken into account by applying a correction to the measured chloride oxidation currents based on a correction curve generated empirically.

For the chloride determination of the invention, the potential of the working electrode may be scanned once from the negative potential limit to the positive potential limit. It is preferred, however, that the working electrode potential be cycled between the negative and positive potential limits a plurality of times to establish a steady-state condition for the working electrode surface, which typically provides more reproducible results. Steady-state of the working electrode surface may be empirically determined to correspond to a specific number of cycles (three, for example), or may be detected by measuring the chloride oxidation current (or other voltammetric feature) for a plurality of voltammetric cycles until successive measured values are equivalent within a predetermined percentage (0.5%, for example).

In the simplest embodiment of the invention, the chloride current parameter used for the chloride determination is equal to the chloride oxidation current measured for one predetermined working electrode potential during one potential scan or cycle. The chloride current parameter used for the chloride determination may also be an average of the chloride oxidation currents measured for one working electrode potential during a plurality of voltammetric cycles, preferably under steady-state electrode conditions.

In a preferred embodiment, the chloride current parameter used for the chloride determination is the average of a plurality of chloride oxidation currents measured for a plurality of predetermined working electrode potentials in a narrow predetermined potential range around a predetermined potential. Improved results may be provided by computer smoothing the chloride oxidation currents in the predetermined potential range, and by averaging the data for multiple voltammograms (3-5, for example).

Improved reproducibility and accuracy for the chloride determination may also be provided by correcting the measured chloride oxidation currents for the background current resulting from other oxidation reactions. In this case, a baseline current measured for a predetermined potential negative of the onset potential for chloride oxidation is subtracted from the measured chloride oxidation current. The baseline current is typically measured at a potential in the range from 0.85 to 1.20 V vs. SSCE/M, depending on the plating bath chemistry. The baseline current measurement is preferably repeated for each chloride current parameter determination.

The invention further provides an apparatus for automated application of the method of the invention. The apparatus comprises a computing device that is interfaced with suitable electronic and mechanical equipment, and includes a memory element with a stored algorithm operative to effect at least the basic steps of the method. The stored algorithm may also be operative to effect the calibration steps of the method. The computing device may comprise a computer with integrated components, or may comprise separate components, a microprocessor and a memory device that includes the memory element, for example. The memory element may be of any suitable type, including computer hard drive, microprocessor chip, read-only memory (ROM) chip, programmable read-only memory (PROM) chip, magnetic storage device, computer disk (CD) and digital video disk (DVD), for example.

The apparatus of the invention for determining the concentration of chloride ion in an acid copper plating bath sample comprises: (1) an electrochemical analysis system that includes a potentiostat, an electrochemical cell, a working electrode comprising a noble metal, a counter electrode, a reference electrode, and a means for flowing the plating bath sample at a constant predetermined flow rate over the surface of the working electrode; (2) a computing device having a memory element with a stored algorithm operative to effect at least the basic steps of the method of the invention, comprising (a) flowing the plating bath sample at a constant predetermined flow rate over the surface of the working electrode, (b) scanning the potential of the working electrode relative to a reference electrode between a predetermined negative potential limit and a predetermined positive potential limit at a predetermined potential scan rate, and (c) measuring at least one chloride oxidation current for at least one predetermined working electrode potential in a predetermined potential range to provide a chloride current parameter; and (3) an interface enabling the computing device to control the electrochemical analysis system so as to perform said steps of the method of the invention.

The stored algorithm of the apparatus of the invention may also be operative to effect the additional steps of the method of the invention, comprising (d) generating a standard curve by repeating the steps of flowing the plating bath sample, scanning the potential of the working electrode and measuring at least one chloride oxidation current for a plurality of chloride standard solutions comprising a background electrolyte of the plating bath sample with different known concentrations of chloride ion, and (e) comparing the chloride current parameter provided in the step of measuring with the standard curve to determine the concentration of chloride ion in the plating bath sample.

Suitable electrochemical analysis systems, computing devices, memory elements, and interfaces for use in the apparatus of the invention are well known to those skilled in the art. In a preferred embodiment, the electrochemical analysis system of the apparatus of the invention further includes a rotation motor for rotating the working electrode, or a pump and suitable plumbing for flowing the plating bath sample over the surface of a stationary working electrode at a constant flow rate.

FIG. 1 shows a schematic representation of a preferred apparatus 100 of the invention. An electronic potentiostat 101 is preferably used to control the potential of a working electrode WE by passing current between working electrode WE and a counter electrode CE so as to drive working electrode WE to a desired potential relative to a reference electrode RE. These three electrodes are immersed in the plating bath sample contained in electrochemical cell 102. Use of potentiostat 101 avoids passing appreciable current through reference electrode RE, which might change its potential. However, the invention may be practiced using any other suitable device for controlling the potential of working electrode WE. The tip of reference electrode RE, or an extension thereof, is preferably located as close as practical to working electrode WE so as to minimize errors in the working electrode potential associated with solution resistance. Most commercial potentiostats include a current follower device (not shown) to avoid errors in the potential of working electrode WE associated with the resistance of the current measuring device.

Preferred apparatus 100 of FIG. 1 also comprises a computing device 103 having a memory element 104 with a stored algorithm for effecting at least the basic steps of the invention, and an interface 105 enabling computing device 103 to control the electrochemical analysis system. Memory element 104 may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. Memory element 104 may be an integral part of computing device 103 or may be a separate device. Interface 105 may be an integral part of computing device 103 or may be a separate device.

As depicted in FIG. 1, preferred apparatus 100 preferably also comprises a rotation motor 106 for rotating working electrode WE, which preferably has a rotating disk configuration. Rotation motor 106 is preferably controlled by computing device 103, either directly or via interface 105 (as shown). Separate interface devices may also be used for the electrochemical analysis system and the rotation motor. Alternatively, preferred apparatus 100 may comprise a pump and suitable plumbing (not shown) for flowing the plating bath sample over the surface of a stationary working electrode WE.

Precise control over the working electrode potential needed for voltammetric measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode may be a reactive metal or an inert metal. Practically any electrical conductor that resists oxidation and reduction in the plating solution may be used as an inert counter electrode, including metals, alloys and conducting oxides. A preferred inert counter electrode material is 316 stainless steel, which is highly oxidation-resistant and relatively inexpensive, but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

The composition of acid copper electroplating baths varies greatly depending on the type of bath and the supplier. High-acid baths typically contain 40-100 g/L copper sulfate, 140-240 g/L sulfuric acid and 25-100 ppm chloride ion. Low-acid baths typically contain 125-200 g/L copper sulfate, 1-40 g/L sulfuric acid and 25-100 ppm chloride ion. Acid copper plating bath additives are generally proprietary formulations supplied in the form of solutions that may contain more than one additive species or combination of additives. The chemical nature and concentrations of the additive species are typically not specified and may be changed from time to time by the supplier without notice.

Description of a Preferred Embodiment

The efficacy of the invention for determining the concentration of chloride ion in an acid copper bath sample was demonstrated for the Low Acid Viaform™ (Enthone, Inc.) acid copper sulfate plating bath. The supporting electrolyte contained 160 g/L $CuSO_4.5H_2O$, 10 g/L $H_2SO_4$, and 30-70 mg/L chloride ion. The background electrolyte comprised the supporting electrolyte with suppressor, accelerator (anti-suppressor) and leveler additives at the concentrations recommended by the bath supplier.

Voltammetric measurements were made under potentiostatic control using a Qualilab QL-10® plating bath analyzer (ECI Technology, Inc.). All potentials are given relative to the SSCE/M (modified silver-silver chloride electrode) reference. The plating bath sample (50 mL) was contained in a polyethylene beaker cell (open to the atmosphere). The working electrode was a 4-mm diameter platinum rotating disk electrode rotated at 2500 rpm and cycled at 2.00 V/s between +0.17 V or −0.10 V and +1.65 V vs. SSCE/M. Reported currents were not corrected for the working electrode area (0.13 $cm^2$). The counter electrode was a stainless steel rod (6 mm diameter). During measurements, the solution temperature was controlled at 25° C. within ±0.1° C.

Figure 2:
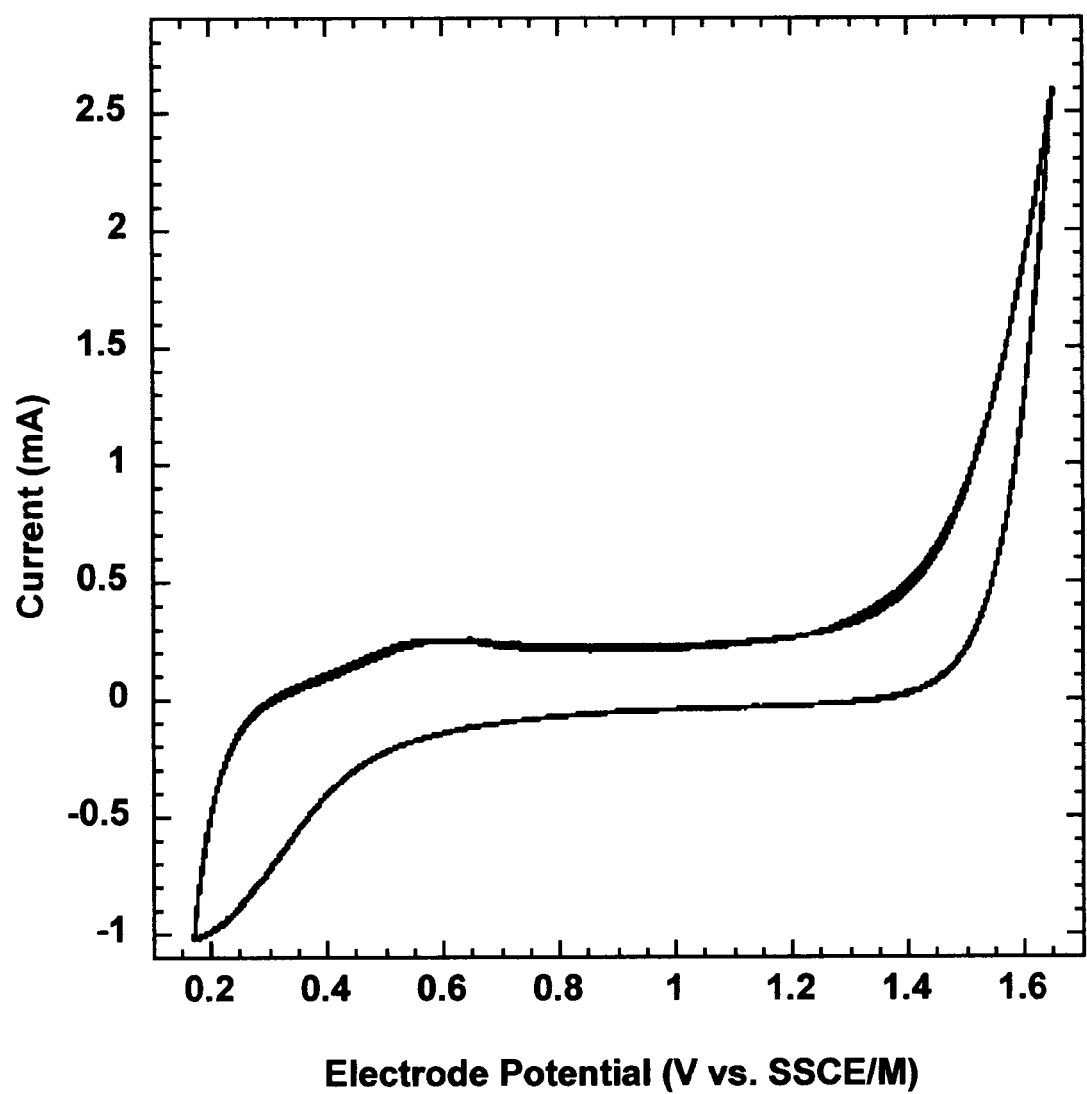
FIG. 2 shows cyclic voltammograms for a platinum rotating disk electrode (2500 rpm) cycled between +0.17 V and +1.65 V at 2.00 V/s in an acid copper sulfate plating bath (25° C.) containing low (30 ppm), target (50 ppm) and high (70 ppm) chloride concentrations.

FIG. 2 shows cyclic voltammograms for the platinum rotating disk electrode (2500 rpm) cycled between +0.17 V and +1.65 V at 2.00 V/s in the acid copper sulfate plating bath (25° C.) containing low (30 ppm), target (50 ppm) and high (70 ppm) chloride concentrations. For this negative potential limit, which is relatively positive, minimal copper plating occurs so that the copper stripping peak normally used for CVS analysis is practically absent. Except for potentials positive of about 1.25 V, at which chloride oxidation and oxygen evolution occur, most of the current is due to double layer charging associated with the relatively high potential scan rate. On this current scale, the chloride oxidation current (positive of 1.25 V) is almost indiscernible as additional current superimposed on the current due to the onset of oxygen evolution.

Figure 3:
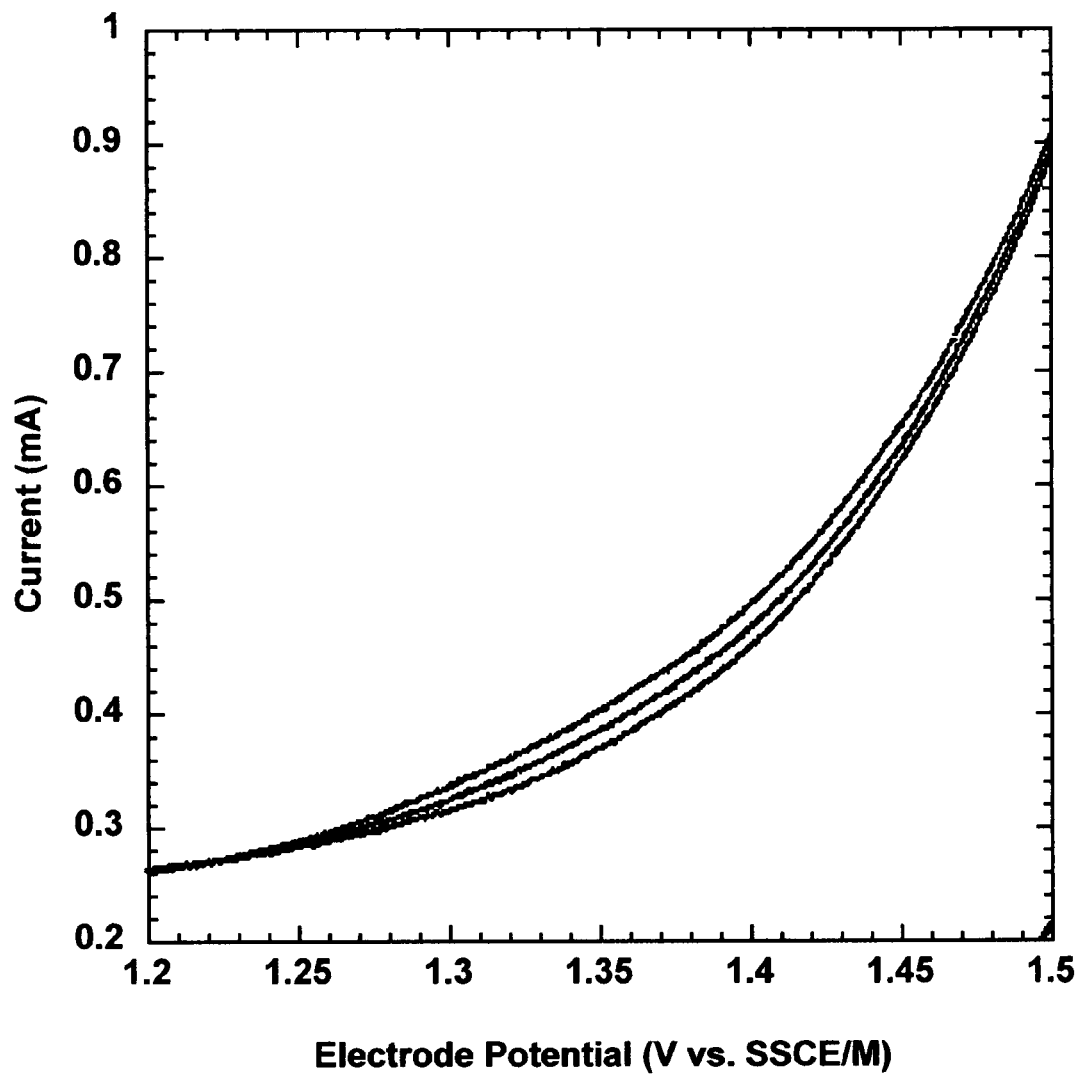
FIG. 3 shows the potential region of the cyclic voltammograms of FIG. 2 in which chloride oxidation occurs.

FIG. 3 shows the potential region of the cyclic voltammograms of FIG. 2 in which chloride oxidation occurs. In this case, the chloride oxidation current, which increases with chloride concentration, is clearly evident as a shoulder at potentials positive of 1.25 V superimposed on the oxygen evolution current. Inspection of these data indicates that chloride oxidation currents may be measured according to the invention in the potential range from 1.3 V to 1.5 V vs. SSCE/M.

Figure 4:
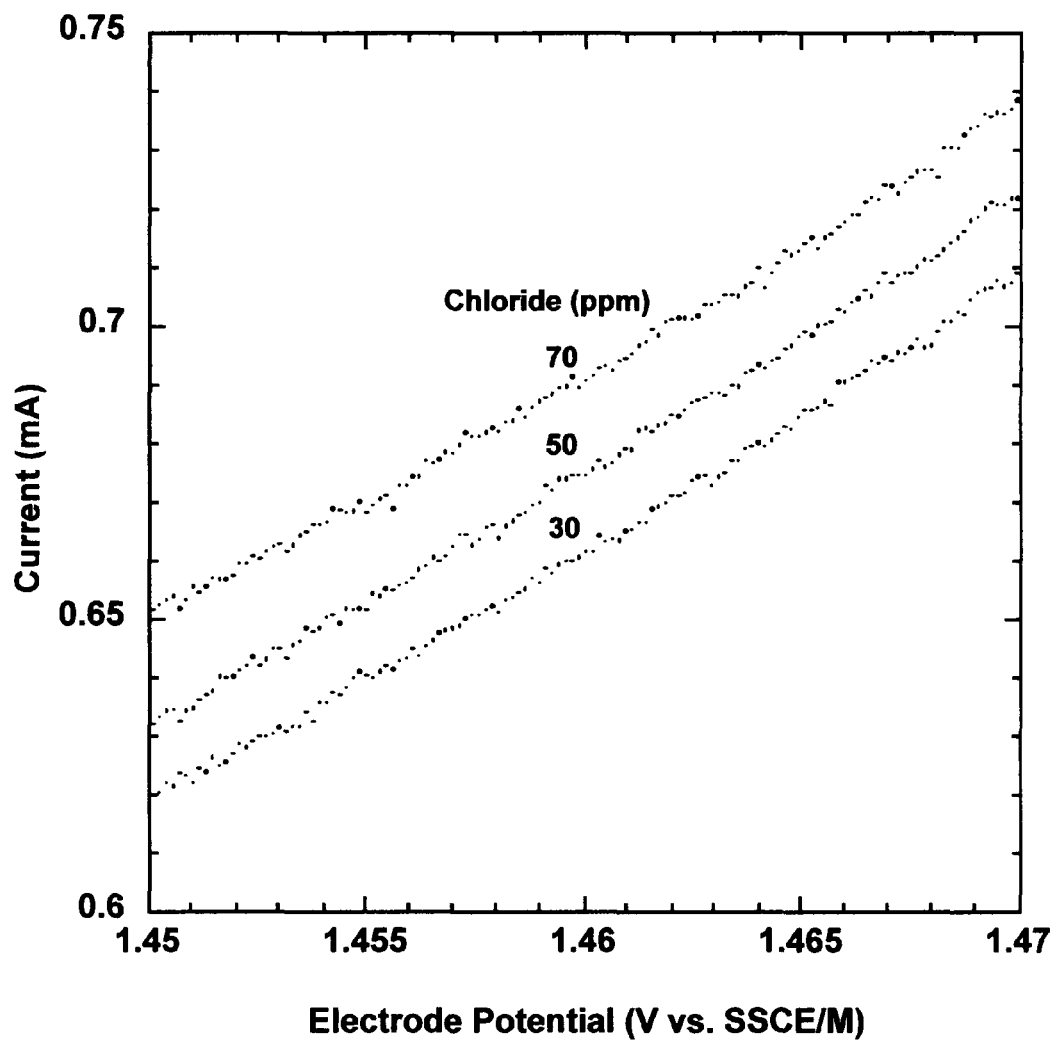
FIG. 4 shows the potential region of the cyclic voltammograms of FIG. 2 in which the chloride current parameter was determined by averaging and smoothing the chloride oxidation currents around 1.46 V vs. SSCE/M.

FIG. 4 shows the potential region of the cyclic voltammograms of FIG. 2 around 1.46 V, at which the chloride current parameter was determined. The linear dependence of the current on chloride concentration is evident. To arrive at the chloride current parameter, the last three out of ten voltammograms were averaged, and the chloride oxidation currents measured for 5-15 points on either side of 1.46 V for the averaged voltammogram were smoothed using available computer software. Note that the potential difference between points was small (0.15 mV) so that the potential was practically 1.46 V for all of the points. The chloride oxidation current for the smoothed data was corrected for background current by subtracting the baseline current measured at 0.85 V vs. SSCE/M.

Figure 5:
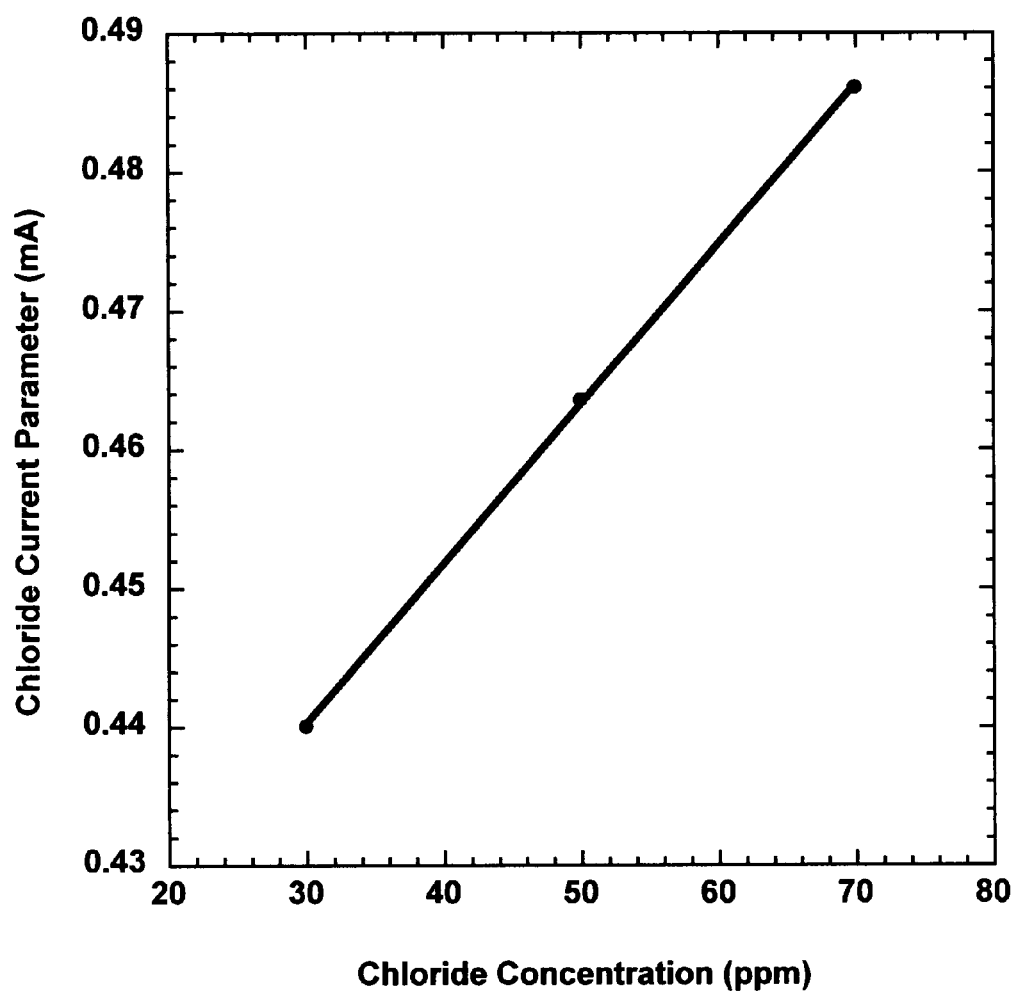
FIG. 5 shows a standard curve of the chloride current parameter as a function of chloride concentration determined from the data of FIG. 4 at 1.46 V vs. SSCE/M.

FIG. 5 shows a standard curve of the chloride current parameter as a function of chloride concentration determined from the data of FIG. 4 at 1.46 V vs. SSCE/M. A good linear correlation is evident, demonstrating the efficacy of the method and device of the invention.

Figure 6:
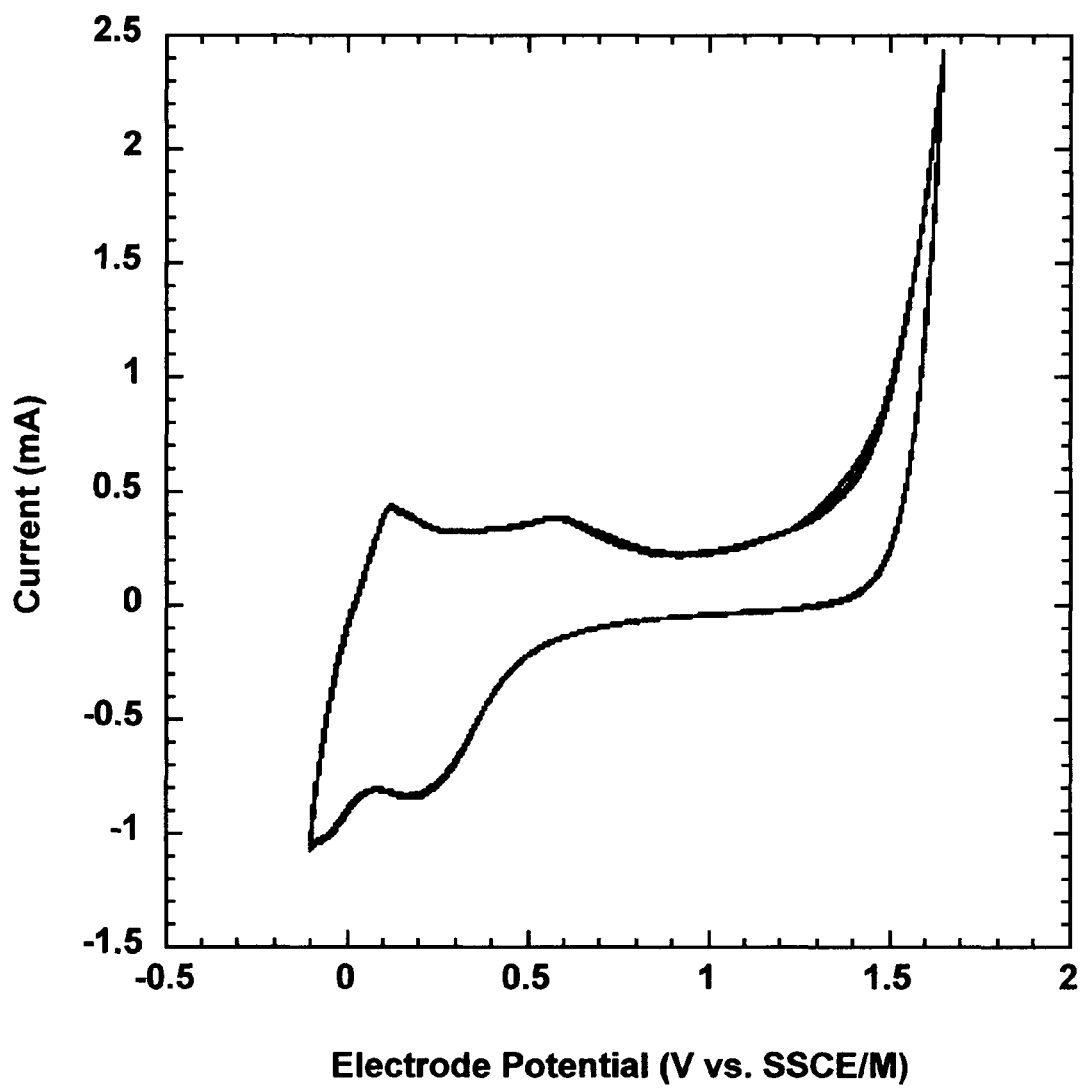
FIG. 6 shows cyclic voltammograms for a platinum rotating disk electrode (2500 rpm) cycled between +0.17 mV and +1.65 V at 2.00 V/s in an acid copper sulfate plating bath (25° C.) containing low (30 ppm), target (50 ppm) and high (70 ppm) chloride concentrations.

FIG. 6 shows cyclic voltammograms analogous to those of FIG. 2 except that the negative potential limit was more negative (−0.10 V instead of +0.17 V). In this case, appreciable plating and stripping of copper is evident as peaks in the negative potential region.

Figure 7:
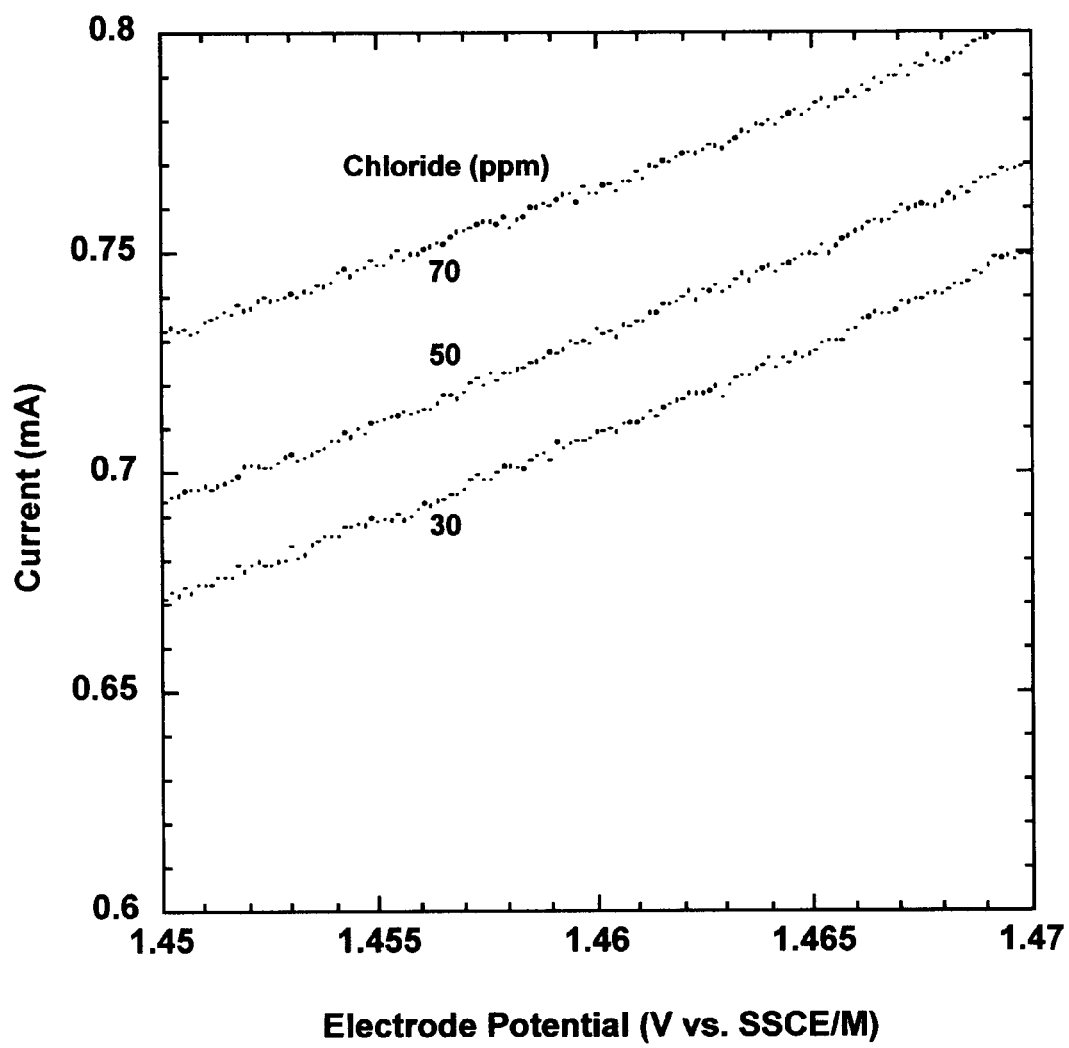
FIG. 7 shows the potential region of the cyclic voltammograms of FIG. 6 in which the chloride current parameter was determined by averaging and smoothing the chloride oxidation currents around 1.46 V vs. SSCE/M.

FIG. 7 shows the potential region of the cyclic voltammograms of FIG. 6 around 1.46 V, at which the chloride current parameter was determined. Some non-linearity in the dependence of the current on chloride concentration is evident. To arrive at the chloride current parameter, these data were subjected to a procedure comparable to that used for the data obtained at the less negative potential limit (+0.17 V).

Figure 8:
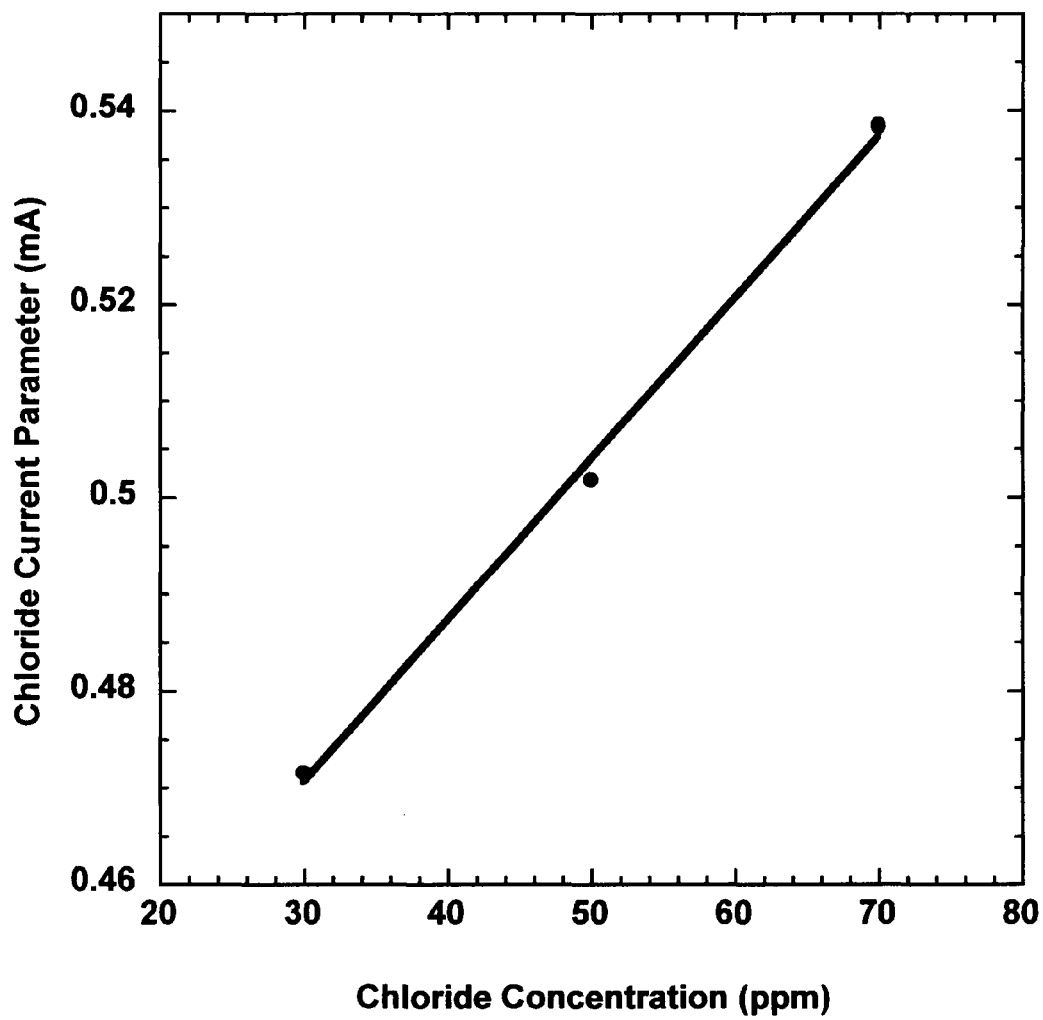
FIG. 8 shows a standard curve of the chloride current parameter as a function of chloride concentration determined from the data of FIG. 7 at 1.46 V vs. SSCE/M.

FIG. 8 shows a standard curve of the chloride current parameter as a function of chloride concentration determined from the data of FIG. 7 at 1.46 V vs. SSCE/M. In this case, linearity is good but not as good as that observed for the less negative potential limit (+0.17 V), which is preferred.

TABLE 1

Comparison of Invented Method and Titration Method for Chloride Determination over Four-Day Period

|  | Invented Method | Titration Method |
| --- | --- | --- |
|  | 50.48 | 49.44 |
|  | 49.49 | 49.20 |
|  | 50.51 | 48.99 |
|  | 50.06 | 50.54 |
|  | 49.87 | 49.75 |
|  | 49.74 | 50.85 |
|  | 49.80 | 49.58 |
|  | 50.32 | 50.69 |
|  | 50.67 | 49.64 |
|  | 49.31 | 49.55 |
|  | 49.90 | 49.64 |
| Average (ppm) | 50.01 | 49.81 |
| Expected (ppm) | 50.00 | 50.00 |
| Accuracy (%) | 0.025 | −0.39 |
| Std. Deviation | 0.44 | 0.61 |
| RSD (%) | 0.87 | 1.23 |

Table I compares chloride analysis results obtained using the method and apparatus of the invention with those obtained using the standard silver nitrate titration method for the Low Acid Viaform™ acid copper plating containing 50 ppm chloride ion. Measurements were made using both methods throughout a four-day period (different times). These data show that the accuracy for the two methods is comparable. However, the method of the invention is much faster and does not generate a waste stream.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining the concentration of chloride ion in an acid copper plating bath sample, comprising the steps of:
    flowing the plating bath sample at a constant predetermined flow rate over the surface of a working electrode comprising a noble metal;
    scanning the potential of the working electrode relative to a reference electrode between a predetermined negative potential limit less negative than −0.15 V versus SSCE/M and a predetermined positive potential limit at a predetermined potential scan rate; and
    measuring at least one chloride oxidation current for at least one predetermined working electrode potential in a predetermined potential range to provide a chloride current parameter,
    wherein the chloride current parameter provides a relative measure of the chloride concentration in the acid copper plating bath sample.

2. The method of claim 1, further comprising the steps of:
    generating a standard curve by repeating the steps of flowing the plating bath sample, scanning the potential of the working electrode and measuring at least one chloride oxidation current for a plurality of chloride standard solutions comprising a background electrolyte of the plating bath sample with different known concentrations of chloride ion; and
    comparing the chloride current parameter provided in the step of measuring with the standard curve to determine the concentration of chloride ion in the plating bath sample.

3. The method of claim 1, wherein the acid copper plating bath sample comprises anions selected from the group consisting of sulfate, fluoroborate, sulfamate, alkylsulfonate, and mixtures thereof.

4. The method of claim 1, wherein the noble metal is selected from the group consisting of platinum, iridium, gold, osmium, palladium, rhenium, rhodium, ruthenium, and alloys thereof.

5. The method of claim 1, wherein the working electrode is a rotating disk electrode and the constant predetermined flow rate is provided by rotating the rotating disk electrode at a constant rate in the range from 100 to 10000 rpm, preferably in the range from 200 to 3000 rpm.

6. The method of claim 1, wherein the constant predetermined flow rate is provided by pumping the plating bath sample at a constant rate in the range from 200 to 300 mL/minute past a stationary working electrode.

7. The method of claim 1, wherein the predetermined positive potential limit is less positive than +1.70 V versus SSCE/M.

8. The method of claim 1, wherein the predetermined potential scan rate is in the range from 1.0 to 4.0 V/second.

9. The method of claim 1, wherein the predetermined potential range for measuring at least one chloride oxidation current is from 1.3 to 1.5 V versus SSCE/M.

10. The method of claim 2, wherein the plating bath sample and the standard solutions are maintained at the same predetermined temperature within at least ±1° C., preferably within less than ±0.5° C., during measurements of the chloride oxidation currents.

11. The method of claim 1, wherein the chloride current parameter used for the chloride determination is the average of a plurality of chloride oxidation currents measured for a plurality of predetermined working electrode potentials in a predetermined potential range.

12. The method of claim 1, further comprising the step of correcting the measured chloride oxidation currents for a background current by subtracting a baseline current measured for a predetermined potential negative of the onset potential for chloride oxidation.

13. A method for determining the concentration of chloride ion in an acid copper plating bath sample, comprising the steps of:

flowing the plating bath sample at a constant predetermined flow rate over the surface of a working electrode comprising a noble metal;

scanning the potential of the working electrode relative to a reference electrode between a predetermined negative potential limit less negative than −0.15 V versus SSCE/M and a predetermined positive potential limit less positive than +1.70 V versus SSCE/M at a predetermined potential scan rate in the range from 1.0 to 4.0 V/second;

measuring at least one chloride oxidation current for at least one predetermined working electrode potential in the potential range from 1.3 to 1.5 V versus SSCE/M to provide a chloride current parameter;

generating a standard curve by repeating the steps of flowing the plating bath sample, scanning the potential of the working electrode and measuring at least one chloride oxidation current for a plurality of chloride standard solutions comprising a background electrolyte of the plating bath sample with different known concentrations of chloride ion; and comparing the chloride current parameter provided in the step of measuring with the standard curve to determine the concentration of chloride ion in the plating bath sample, wherein the plating bath sample and the standard solutions are maintained at the same predetermined temperature within less than ±0.5° C. during measurements of the chloride oxidation currents.

14. An apparatus for determining the concentration of chloride ion in an acid copper plating bath sample, comprising:

an electrochemical analysis system that includes
  a potentiostat,
  an electrochemical cell containing the plating bath sample,
  a working electrode comprising a noble metal,
  a counter electrode,
  a reference electrode, and
  a means of flowing the plating bath sample at a constant predetermined flow rate over the surface of the working electrode;

a computing device having a memory element with a stored algorithm operative to effect the steps of the method of the invention, comprising flowing the plating bath sample at a constant predetermined flow rate over the surface of the working electrode, scanning the potential of the working electrode relative to a reference electrode between a predetermined negative potential limit less negative than −0.15 V versus SSCE/M and a predetermined positive potential limit at a predetermined potential scan rate, and measuring at least one chloride oxidation current for at least one predetermined working electrode potential in a predetermined potential range to provide a chloride current parameter; and an interface enabling the computing device to control the electrochemical analysis system so as to perform said steps of the method of the invention.

15. The apparatus of claim 14, wherein the stored algorithm is operative to effect additional steps of the method of the invention, comprising generating a standard curve by repeating the steps of flowing the plating bath sample, scanning the potential of the working electrode and measuring at least one chloride oxidation current for a plurality of chloride standard solutions comprising a background electrolyte of the plating bath sample with different known concentrations of chloride ion, and comparing the chloride current parameter provided in the step of measuring with the standard curve to determine the concentration of chloride ion in the plating bath sample.

16. The apparatus of claim 15, wherein the stored algorithm is operative to effect the additional step of the method of the invention, comprising correcting the measured chloride oxidation currents for a background current by subtracting a baseline current measured for a predetermined potential negative of the onset potential for chloride oxidation.

17. The apparatus of claim 14, wherein the working electrode is a rotating disk electrode and the means of controlling flow of the plating bath sample over the working electrode surface is a rotation motor for rotating the rotating disk electrode at a constant rate.

18. The apparatus of claim 14, wherein the working electrode is a stationary electrode and the means of controlling flow of the plating bath sample over the working electrode surface is a pump for pumping the plating bath sample at a constant rate.

19. The apparatus of claim 14, wherein the memory element is selected from the group consisting of computer hard drive, microprocessor chip, read-only memory (ROM) chip, programmable read-only memory (PROM) chip, magnetic storage device, computer disk (CD) and digital video disk (DVD).

* * * * *